(12) United States Patent
Zurlo et al.

(10) Patent No.: US 7,879,332 B2
(45) Date of Patent: *Feb. 1, 2011

(54) ULTRA-HIGH YIELD INTRAVENOUS IMMUNE GLOBULIN PREPARATION

(75) Inventors: Gene Zurlo, Kiawah Island, SC (US); Dennis Curtin, Peru, NY (US); Allan L. Louderback, Temple City, CA (US)

(73) Assignee: Plasma Technologies, LLC, Kiawah Island, SC (US)

( * ) Notice: Subject to any disclaimer, the term of this patent is extended or adjusted under 35 U.S.C. 154(b) by 686 days.

This patent is subject to a terminal disclaimer.

(21) Appl. No.: 11/358,431

(22) Filed: Feb. 21, 2006

(65) Prior Publication Data

US 2007/0049734 A1   Mar. 1, 2007

Related U.S. Application Data

(63) Continuation-in-part of application No. 11/232,527, filed on Sep. 22, 2005, which is a continuation-in-part of application No. 11/217,956, filed on Sep. 1, 2005.

(51) Int. Cl.
*A61K 39/395* (2006.01)

(52) U.S. Cl. ............... 424/177.1; 424/176.1; 424/93.7; 424/520

(58) Field of Classification Search .................. None
See application file for complete search history.

(56) References Cited

U.S. PATENT DOCUMENTS

| | | | |
|---|---|---|---|
| 2,390,074 A | 12/1945 | Cohn | |
| 4,067,863 A | 1/1978 | Watt | |
| 4,093,606 A | 6/1978 | Covel | |
| 4,126,605 A | 11/1978 | Schneider et al. | |
| 4,136,094 A | 1/1979 | Condie | |
| 4,154,819 A | 5/1979 | Stephan | |
| 4,165,370 A | 8/1979 | Coval | |
| 4,246,085 A | 1/1981 | Mattock | |
| 4,296,027 A | 10/1981 | Condie | |
| 4,312,949 A | 1/1982 | Ahreus | |
| 4,318,902 A | 3/1982 | Stephan | |
| 4,321,192 A | 3/1982 | Jain | |
| 4,322,403 A | 3/1982 | Bunnig | |
| 4,347,138 A | 8/1982 | Ohno et al. | |
| 4,371,520 A | 2/1983 | Uemura et al. | |
| 4,476,109 A | 10/1984 | Kimura et al. | |
| 4,486,282 A * | 12/1984 | Bier | ........................ 204/529 |
| 4,624,780 A | 11/1986 | Chang | |
| 4,639,513 A | 1/1987 | Hou et al. | |
| 4,675,384 A | 6/1987 | Dromard et al. | |
| 4,692,331 A | 9/1987 | Uemura et al. | |
| 4,835,257 A | 5/1989 | Friedrich-Fiechtl | |
| 4,877,866 A | 10/1989 | Rudnick et al. | |
| 5,177,194 A | 1/1993 | Sarno et al. | |
| 5,310,877 A | 5/1994 | Spencer | |
| 5,561,115 A | 10/1996 | Tenold | |
| 6,093,324 A | 7/2000 | Bertolini et al. | |
| 6,281,336 B1 | 8/2001 | Laursen et al. | |
| 6,307,028 B1 | 10/2001 | Lebing et al. | |
| 6,402,913 B1 | 6/2002 | Gilbert et al. | |
| 6,485,932 B1 | 11/2002 | McIntosh et al. | |
| 6,835,379 B2 | 12/2004 | Andersson et al. | |
| 6,875,848 B2 | 4/2005 | Debart et al. | |
| 6,881,573 B2 | 4/2005 | Louderback | |
| 6,893,639 B2 | 5/2005 | Levy et al. | |
| 2001/0051708 A1 | 12/2001 | Laursen et al. | |
| 2002/0151688 A1 | 10/2002 | Debart et al. | |
| 2003/0022149 A1 | 1/2003 | Shanbrom | |
| 2003/0036638 A1 | 2/2003 | Joergensen et al. | |
| 2003/0129167 A1 | 7/2003 | Shanbrom | |
| 2005/0020816 A1 | 1/2005 | Joergensen et al. | |

OTHER PUBLICATIONS

Joergen Dam, Plasma Fractionation based on Chromatography and Precipitation by Polyethylene Glycol and Caprylic Acid, A report from the first Plasma Products Biotechnology Meeting, 17-18 (Mar. 27-30, 1999, Daydream Island Queensland Australia), http://ebiotrade.com/GE/AKTAclub7/1.PDFs/DS3118114075.pdf.

* cited by examiner

*Primary Examiner*—Michael Szperka
*Assistant Examiner*—Yunsoo Kim
(74) *Attorney, Agent, or Firm*—Fish & Associates, PC

(57) ABSTRACT

An efficacious large-scale alcohol-free plasma fractionation production process which produces a high-yielding, non-denatured, double viral-inactivated intravenous human immune gamma globulin (IgG) product. The process employs one or more salts from a group of salts comprising sodium citrate, sodium acetate, sodium gluconate, ammonium sulfate, sodium chloride, sodium sulfate and ammonium chloride in two initial fractionation steps, followed by diafiltration to remove those salts employed. A process which employs alcohol via the process of the disclosed inventive method is also disclosed.

12 Claims, 4 Drawing Sheets

ULTRA-HIGH YIELD INTRAVENOUS IMMUNE GLOBULIN PREPARATION

CONTINUATION-IN-PART

This application for patent is a Continuation-in-Part of U.S. patent application Ser. No. 11/232,527 titled AN ULTRA-HIGH YIELD INTRAVENOUS IMMUNE GLOBULIN PREPARATION and filed Sep. 22, 2005 which is a Continuation-in-Part of U.S. patent application Ser. No. 11/217,956, titled AN ULTRA-HIGH YIELD INTRAVENOUS IMMUNE GLOBULIN PREPARATION and filed Sep. 1, 2005.

FIELD OF INVENTION

This invention relates generally to methods for immune serum globulin purification, and, more particularly, to methods for alcohol-free separation of immune globulin from blood plasma or other blood based material. Interestingly, the method of the instant invention also may be employed using alcohol.

BACKGROUND AND DESCRIPTION OF RELATED ART

Commonly, contemporary methods for separation of immune globulins (IgG) from blood plasma or other blood based material depend upon early work by Edwin J. Cohn. As found in U.S. Pat. No. 5,177,194 issued Jan. 5, 1993 to Maria E. Sarno, et al. (SARNO), "One scheme in widespread use is the well-known Cohn fractionation method, which is based on differential precipitation using cold ethanol." Cohn et al. *J. Am. Chem. Soc.* 68, 459 (1946).

A U.S. Pat. No. 2,390,074 issued Dec. 4, 1945 to Edwin J. Cohn (Cohn) disclosed use of alcohol, acetone and dioxane as precipitants in such fractionation processes. Continued dependence upon alcohol as a precipitant is further demonstrated in U.S. Pat. No. 6,893,639 B2 issued May 17, 2005 to Joshua Levy, et al. (Levy), wherein it is stated, "The conventional industrial methods of immune globulins purification from blood plasma are based on cold ethanol fractionation which co-precipitate groups of proteins based on their isoelectric points at given alcohol concentration at sub-zero temperatures."

Cohn's work was stimulated by the need of the military for a stable solution for use as a plasma volume expander during World War II to replace lyophilized plasma. Consequently, the Cohn method focused on optimizing the process for separating the albumin fraction which provides the osmolality necessary for plasma volume expansion.

Even so, the use of alcohol precipitants is not without difficulties, as illustrated by Cohn, "Some protein precipitants, such as alcohol, have a tendency to denature many proteins with which they come in contact, the danger of denaturation increasing with concentration of the alcohol and increase in temperature. For many proteins, it has been found advisable to exercise considerable care in mixing the precipitant with the plasma or other protein solution in order to avoid denaturation of the protein." For this reason, it is considered prudent to provide an alcohol-free method for blood plasma and other blood based material fractionation, including IgG purification.

Further considerations of combining ethanol and water may be warranted relative to denaturation of proteins. For example, if one adds 500 ml of ethanol (100%) to 500 ml of water, one does not obtain 1000 ml of 50% ethanol. Rather, the final volume is approximately 956 ml. It is surmised that the reduction in volume is due to a tight binding between the ethanol and water molecules. Such binding may be a cause of changes in protein configuration resulting in some permanent denaturation of protein molecules which remains after ethanol is removed and water is returned.

In the 1970's, chromatography was found to be useful in the separation and purification of plasma proteins. Chromatography separates plasma proteins by specifically targeting unique characteristics of each, including molecular size (gel filtration), charge (ion exchange chromatography), and known interactions with specific molecules (affinity chromatography).

The use of various chromatographic methods on an industrial scale has been adopted for the isolation of small-weight, high-value proteins, such as Factor VII, from plasma, and for the final purification of gamma globulin after separation from the plasma by Cohn, or modified Cohn methodologies. However, chromatographic separation of the large-weight, lower-value fractions such as albumin and gamma globulin, on an industrial scale has not been found to be practical.

Two U.S. patent applications, filed by Edward Shanbrom, having Application Numbers 20030022149 (Shanbrom '149) and 20030129167 (Shanbrom '167) filed Jan. 30, 2003 and Jul. 10, 2003, respectively, teach of use of carboxylic salts (e.g., trisodium citrate) as an agent for enhancing formation of a cryoprecititate from plasma The method(s) of Shanbrom generally involve trisodium citrate and other citrate salts as agents for enhancing production of blood clotting factors from cryoprecipitate.

Shanbrom '149 teaches in paragraph 0009 that "It is an object of the present invention to provide enhanced yields of cryoprecipitate." Shanbrom also teaches, in paragraph 0011, that carboxylic acids are effective agents for enhancing the production of blood clotting factors from the cryoprecipitate. Shanbrom '149 notes that the addition of citrate to plasma, especially at concentrations between two and ten percent, by weight, does not appreciably denature labile proteins. Moreover, it is noted in Shanbrom '149 that citrate potentiates or enhances the killing of microorganisms by heat treatment.

Shanbrom '167 notes in paragraph 0015 that, "Not only does added citrate increase the amount of cryoprecipitate, it simplifies the process by decreasing the requirement for freezing . . . " plasma in order to harvest cryoprecipitate. Shanbrom clearly teaches use of production of a cryoprecipitate for the purpose of fractionating products from the cryoprecipitate through the use of trisodium citrate in concentrations of two to ten percent.

While Shanbrom '149 and '167 deal directly with extracting labile coagulation products from a cryoprecipitate formed through use of citrate compounds, particularly trisodium citrate, and with killing microorganisms in the cryoprecipitate using the citrate compounds, the instant invention deals directly with extracting non-labile products (e.g., albumin, gamma globulin and alpha-1-antitrypsin) from a supernatant formed through use of salt compounds. Shanbrom neither teaches nor addresses using a supernatant in any way.

In the 1950's, it was discovered that a "cryoprecipitate" derived from blood-based material, contained various factors was useful in treating clotting disorders such as hemophilia Such a cryoprecipitate, as the name implies, was obtained by freezing blood plasma followed by controlled thawing at zero to four degrees Centigrade to form a liquid suspension of the precipitate. A supernatant derived from the cryoprecipitating process was then available for fractionation using methods according to Cohn to produce albumin and gamma globulin. Subsequent developments led to fractionation of cryoprecipitate into pure concentrates of Factor VIII, von Willebrand Factor, and other clotting factors. Such may be accomplished by using non-alcoholic separations and chromatographic purification.

BRIEF SUMMARY AND OBJECTS OF THE INVENTION

In brief summary, this instant invention provides novel and effective methods of isolating gamma globulin from plasma and formulating it into an intravenous injectable preparation. Accordingly, this invention, which may be defined to be "an ultra-high yield intravenous immune globulin preparation," achieves higher yields of a superior quality gamma globulin by directly and expeditiously separating the gamma globulin from the plasma by means of a non-denaturing precipitant, which may be selectively chosen from a group of organic salts including sodium citrate, sodium acetate, and sodium gluconate and from a group of inorganic salts including ammonium sulfate, sodium chloride, sodium sulfate and ammonium chloride. Two surprising characteristics of use of these salts are that (1) fractionation depends upon employing an effective weight percentage solution and (2) that these salts are effective in such fractionation when used alone and when used in a combined mixture of two or more salts wherein the combination has the same effective weight percentage.

Also, addition of these salts to protein in solution proves to be not as reactive to removal of water as addition of ethanol by previous methods. A rapid isolation using these salts, removal of the resulting fraction followed by removal of salt from the resulting fraction and a quick restoration of the internal water molecule of the protein has proved superior to ethanol fractionation using currently employed methods.

The inventive process is for fractionating blood-based products to produce a useful, non-denatured immunoglobulin (sometimes referred to as IgG) product which involves the following critical steps:

(a) adding a sufficient first measure of a chosen salt or combination of salts to a quantity of blood-based material to be fractionated to bring the added first chosen salt or combination of salts to a first predetermined concentration level which forms a supernatant product, free of euglobulins, the supernatant being separable from a residual paste and separating the two;

(b) performing a second fractionation step by adding a second measure of the same or another chosen salt or combination of chosen salts to the separated supernatant product to bring the chosen salt or salts combination to a second predetermined concentration level which, thereby, forms a second separable product which is a paste and a second residual product which is a supernatant, the products thereafter being separated;

(c) forming a liquid dilution of the second separated paste product; and (d) diafiltering the second separated and liquified paste product to form a low volume resulting product which is substantially free of the chosen salt or salts and ready for processing by currently known and practiced procedures to complete production of the useful, non-denatured IgG.

In step (a), the first volume utilizes an added concentrated salt solution or addition of dry salt to the blood-based material to yield an eleven to thirteen percent solution by weight when mixed into a quantity of blood-based material. At this concentration, the added salt selectively dehydrates portions of the blood-based material to form a supernatant and a precipitated residual paste. Note that the supernatant has a resulting salt concentration in the range of eleven to thirteen percent concentration by weight of the selected salt or combination of salts. Preferably the concentration should approximate twelve percent. If desired, the residual paste may be further fractionated into blood factors including VIII, IX, von Willebrand and fibrinogen. Separation of the products may be accomplished by centrifuging or existing methods which are well known in chemistry art. The supernatant is retained for further processing.

In step (b), the second volume utilizes addition of more concentrated salt solution or addition of a sufficient amount of dry salt to the retained supernatant to selectively dehydrate portions thereof to yield a second paste product and a residual second supernatant product. The total concentration by weight of both the second paste and second supernatant should be in a range of approximately twenty-one to twenty-three percent. It is preferred that concentration by weight of the selected salt or combination of salts should approximate twenty-two percent. As with step (a), if desired, the residual (in this case the second supernatant) may be further processed into a group of components comprising albumin, alpha-1-antitrypsin and other proteins. The products may be separated by centrifuging, filtering or other methods which are well-known in the chemistry art.

Surprisingly, precipitation using salts does not appear to be dependent upon some sort of molar reaction. Rather, precipitation appears to be based upon a simple percentage by weight relationship in both steps (a) and (b). In the following table (Table I), effective concentrations of both organic and inorganic salts are found. Note the effective concentration by weight is the substantially the same percentage for each salt listed.

TABLE I

Examples of effective concentration of salts which may be used in Steps (a) and (b).

|  | Molecular Weight | Molar Weight in a 12% Solution (for step (a)) | Molar Weight in a 22% Solution (for step (b)) |
|---|---|---|---|
| Organic Salts |  |  |  |
| Sodium citrate | 294 | 0.408M | 0.748M |
| Sodium acetate | 82 | 1.46M | 2.68M |
| Sodium gluconate | 218 | 0.427M | 0.783M |
| Inorganic Salts |  |  |  |
| Ammonium sulfate | 132 | 0.908M | 1.66M |
| Sodium chloride | 58.5 | 2.05M | 3.76M |
| Sodium sulfate | 142 | 0.845M | 1.54M |
| Ammonium chloride | 53.5 | 2.24M | 4.11M |

Also, surprisingly, the above listed salts may be used in any combination if the total concentration by weight is maintained as cited for steps (a) and (b).

In step (c), it is preferred to dilute the paste product with water having approximately four times the weight of the paste product, although other volumes of water may be judiciously selected within the scope of the invention.

In step (d) a diafiltration system with a 30 KD filtering membrane may be used to separate the selected salt or salts and excess water from the resulting product to permit further processing on an industrial scale. Note, that such filtering is made facile and possible by extracting euglobulins from the supernatant in step (a). As used herein, euglobulins are defined to be those globulins which are insoluble in water, but are soluble in saline solutions. Most importantly, if euglobulins are not removed from a solution and if the ionic strength of that solution is lowered towards deionized water (e.g., in the case of the instant invention), euglobulins foul a diafiltration system, thereby rendering it unuseable.

It is well-known that sodium citrate, has long been used in low concentrations during the collection, preservation and storage of blood plasma. Subsequent diafiltration after use of high concentrations of sodium citrate and/or other salts as a precipitant substantially reduces the ionic strength and volume of the gamma globulin solution, permitting the achievement of chromatographic purification on an industrial scale.

Following separation of gamma globulin from plasma by this method, albumin and alpha-1-antitrypsin are subsequently removed from the remaining proteins by methods available from Cohn or others. The process, according to the instant invention, enables the separation of gamma globulin without exposing it to the denaturing effects of ethanol used in the Cohn process, hence leaving the gamma globulin in a native state. The denaturing effects of alcohol include the formation of polymers, aggregates and fragments of the gamma globulin molecule. However, the use of single or combinations of earlier named selected salts stabilizes the plasma while bringing about precipitation of substantially all of the coagulation proteins, thus preventing the generation of enzyme activators and proteolytic enzymes.

The absence of the denaturing effects of ethanol, the stabilization of the plasma with the selected salts, and the subsequent removal of coagulation proteins by means of the selected salts results in a gamma globulin preparation which has very low anti-complementary activity.

In summary, the process of the instant invention employs high concentrations of one or more preselected salts combined with subsequent removal of those salts from the gamma globulin concentrate by means of diafiltration, a technique which became practical on an industrial scale in the 1980's. Final purification of the resulting gamma globulin is then practically and effectively achieved through the use of well-established chromatographic purification techniques. The invention reduces production costs as a result of higher yields, fewer fractionation steps, shorter overall processing time, lower energy costs, and lower chemical costs. Capital costs are less because of reduced space requirements, reduced work-in-process, reduced processing time, and elimination of the explosion-proof environments required for ethanol processing.

Surprisingly, the method of the instant invention may employ alcohol in concentrations similar to concentrations of salts mentioned supra. While concerns of denaturization exists with the use of ethanol, results of experiments were interesting. A basic difference between historical ethanol procedures is rapid removal of ethanol after completion of the procedure according to the method of the current invention which results in lower denaturization and higher yields than prior intravenous gamma globulin than current ethanol procedures. Also, the alcohol procedure according to the present invention may be run at temperatures which range from zero to twenty-five degrees Centigrade.

Accordingly, it is a primary object to provide an effective intravenous gamma globulin preparation at a cost which is reduced from methods in current practice.

It is therefore a principle object to provide an alcohol-free method for preparing gamma globulin.

It is an important object to provide such a method and preparation which is high-yielding.

It is a further object to provide a gamma globulin preparation which can be rapidly infused with greater patient tolerance than gamma globulin produced by traditional methods employing alcohol.

It is an object to provide a previously unused method employing alcohol which produces a high yield and lower denaturization than contemporary procedures.

It is an object to produce gamma globulin having reduced in-process formation of polymers, aggregates, fragments, enzyme activators and proteolytic enzymes compared with similar preparations produced using traditional alcohol-based methods.

It is a further object to derive a cryoprecipitate as an optional method according to the instant invention to form a liquid suspension of a cryoprecipitate from which, through fractionation, Factor VIII, von Willebrand Factor, and other clotting factors are produced.

These and other objects and features of the present invention will be apparent from the detailed description taken with reference to accompanying drawings.

DETAILED DESCRIPTION OF THE ILLUSTRATED EMBODIMENTS

Reference is now made to flow path elements illustrated in FIGS. 1-4. Generally, each rectangular box is used to illustrate a procedural step; each diamond is used to demonstrate a separation step; each elliptical cylinder designates a product resulting from a preceding procedural or separation step; and each circle is used to identify either a starting point or an off-sheet continuation path point.

Figure 1:
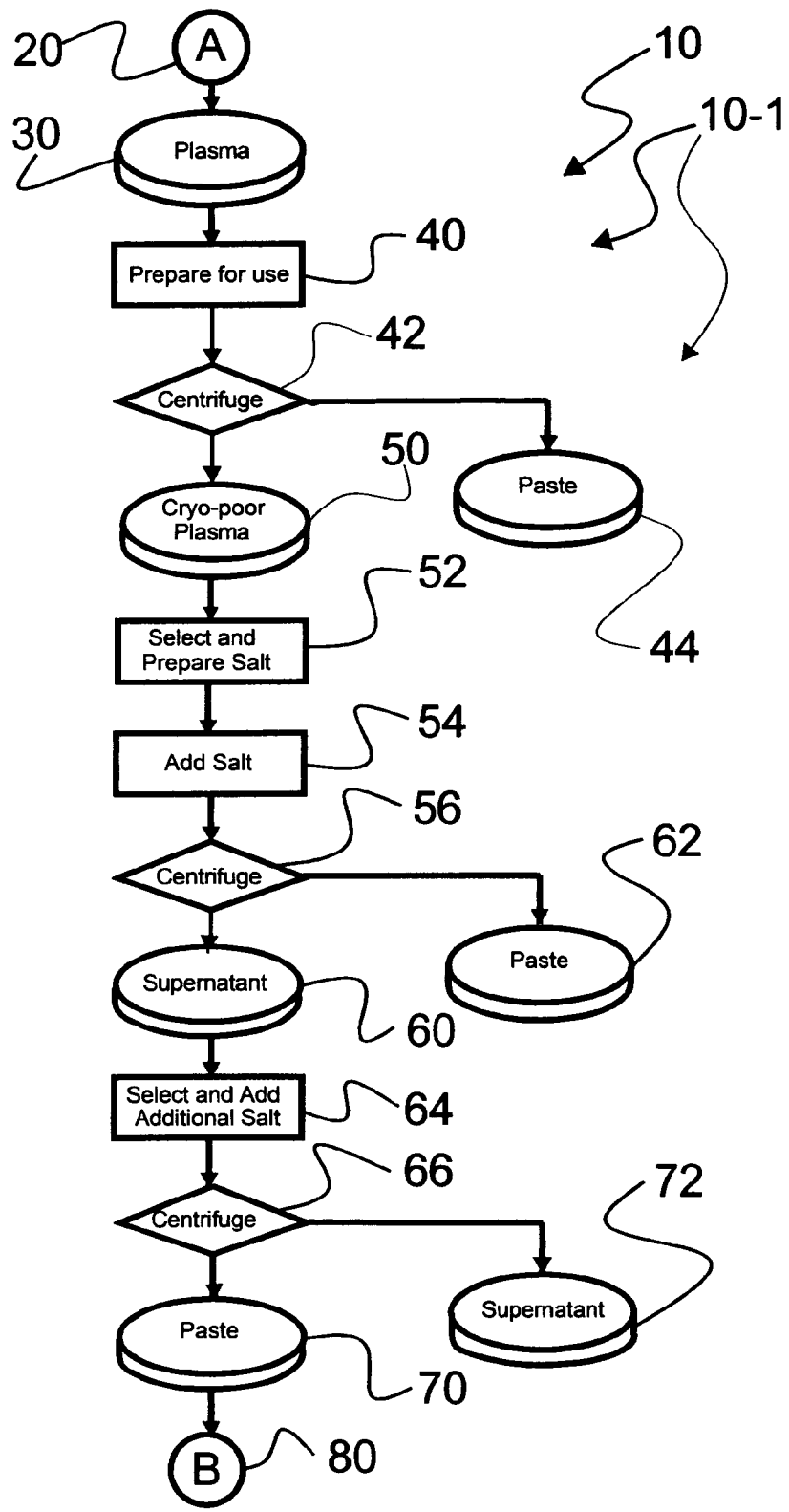
FIG. 1 is a flow diagram of a critical set of initial steps associated with the process according to the instant invention.

Reference is now made to FIG. 1 wherein an initial portion 10-1 of a preferred IgG process flow path, generally numbered 10, is seen. As indicated after initial starting point 20, a volume of plasma 30 to be processed is selected for processing. It should be noted that while plasma 30 is used by example in this description of an illustrated embodiment, other blood-based products may be processed within the scope of the instant invention. Also, after preparation for use, a separation step 42 is used to separate a paste 44 from prepared cryo-poor plasma 50, as is disclosed in more detail hereafter.

As part of procedure 40, selected frozen plasma 30 is warmed to approximately five degrees Centigrade to form a prepared plasma. While five degrees is the target plasma 30 process temperature, which should be maintained throughout the following steps in process 10, a temperature range between limits of two to eight degrees may be held within the scope of the instant invention. Plasma 30 may be used directly if not selected in a frozen state (e.g., thawed during the process of removing a cryogenic precipitate by customary methods).

A quantity of a salt or salts (which may be selected from salts listed in Table I, provided supra) is selected for addition to plasma 50 per procedure 52. Due to the fact that a single salt or a combination of salts may be selected and used, it is prudent to consider an added salt quantity as "at least one salt," as a quantity used may contain a single salt or a combination of salts in each of steps (a) and (b), recited supra.

Generally, a salt or combination of salts may be prepared in solution, added as dry salt or added as a combination of hydrated and dry salts (procedure 54). In any event, it is most important to bring the total concentration of added salts to a predetermined concentration by weight.

As an example, when sodium citrate is selected and used, a fifty percent sodium citrate solution is prepared by stirring five hundred grams of sodium citrate into six hundred milliliters of purified water. Stirring time should be thirty to sixty minutes or, alternately, until the sodium citrate is dissolved. At this point, dilute the mixture with pure water to one thousand milliliters. Add 50% citric acid solution to the mixture until a pH of 7.0 is reached.

As is well known in organic chemistry art, the following steps can be used to produce a fifty percent citric acid solution. Add 50 gm of citric acid to 60 ml of purified water. Stirring time should be about 30 minutes or until the citric acid is in solution. After the citric acid is in solution, add enough purified water to bring the volume to 100 ml and mix well. A portion of this solution, added to the 1000 ml of sodium citrate, adjusts the pH to 7.0. Therefore, add the citric acid to the sodium citrate solution until the pH of 7.0 is reached. It should be noted that a very little citric acid needs to be added to adjust to a pH of 7.0.

Preparatory to performing the first fractionation step (procedure 54 for sodium citrate), a volume of fractionation solution to be added to plasma 50 is calculated. It is a goal that the salt concentration (in this case sodium citrate fractionation solution) should be twelve percent by weight. Also the pH of the fractionation solution should be approximately 7.0.

The formula, (Formula I) for calculating respective volumes of fractionation solution (sodium citrate) and plasma 50 are as follows:

$$x = (C*V)/(0.5-C)$$

where: x is desired volume of 50% sodium citrate solution; C is a desired fractional concentration by weight of sodium citrate; (e.g., 0.12 or twelve percent): and V is volume of solution to be diluted, (e.g., volume of plasma 50).

An example of a calculation by Formula I is:

For a volume ($V_p$) of plasma 50 of 500 liters, and the desired fractional concentration by weight of sodium citrate is twelve percent:

$$x = (0.12*500)/(0.5-0.12) = 158 \text{ liters}$$

Solving Formula I for C yields Formula II into which values of volumes of plasma 50 and sodium citrate may be inserted as follows:

$$C = (0.500*158)/(500+158) = 0.12$$

For procedure 54, over a period of approximately five minutes, add the prepared sodium citrate fractionation solution (which may be at room temperature, i.e. approximately twenty degrees Centigrade) to plasma 50, which has a starting temperature of five degrees Centigrade. Gently stir while adding the sodium citrate solution. Once the sodium citrate solution is completely added to plasma 50, continue gently stirring the resulting slurry for approximately sixty minutes while reducing the slurry temperature to within a range of two to eight degrees Centigrade. (The slurry should maintain pH at approximately 7.0 to 7.1.)

Upon completion of procedure 54, centrifuge as procedure 56. It is recommended that a flow-through centrifuge (e.g., a Westphalia Centrifuge) be used to separate component parts of the slurry into a supernatant liquid 60 and a paste 62 by normal procedures for those skilled in the art, while maintaining temperature of the slurry in the range of two to eight degrees Centigrade.

While supernatant liquid 60, which contains virtually all of the IgG of the original plasma, is retained for further processing as an integral part of the instant inventive method, paste 62 may be further processed to recover blood factors, including Factors VIII, IX, von Willebrand and fibrinogen.

For the second fractionation phase using sodium citrate, perform process step 64 which adds additional sodium citrate fractionation solution to supernatant liquid 60. Enough fifty percent sodium citrate is added to liquid 60 to increase concentration by weight of sodium citrate from twelve percent to twenty-two percent. Note that, for other salt or salts used in step 64, the total concentration by weight of the at least one salt used should be in a range of twenty-one to twenty-three percent, preferably in the range of twenty-two percent.

To calculate the volume of fifty percent sodium citrate to be added, Formula III is provided as follows:

$$C_e = ((V_{60}*C_{60}) + (V_x*C_{0.50}))/(V_{60}+V_x)$$

Where $C_e$ is the desired end concentration by weight of sodium citrate; $V_{60}$ is the volume of supernatant liquid 60; $C_{60}$ is sodium citrate concentration in supernatant liquid 60; $V_x$ is volume of fifty percent sodium citrate to be added; and $C_{50}$ is concentration of fifty percent sodium citrate (i.e. 0.50).

Note that the desired end concentration by weight of sodium citrate in solution is 0.22 or twenty-two percent.

Solving for $V_x$ yields Formula IV which may be used to calculate volume of sodium citrate to be added.:

$$V_x = V_{60}*(C_e-C_{60})/(C_{0.50}-C_e)$$

As an example, for a volume of $V_{60}$ of 552 liters; a concentration by weight of $C_e$ of 0.22; a concentration by weight of 0.12 for $C_{60}$; and a concentration by weight of 0.50 for $C_{0.50}$:

$$V_x = 197 \text{ liters}$$

After adding volume $V_x$ of sodium citrate, stir for two to four hours (though one to two hours is often sufficient for smaller volumes) while retaining the temperature of this mixture between two and eight degrees Centigrade. Note that this solution will change color to a pale yellow as the additional sodium citrate is added and the mixture is stirred.

After stirring, per step 66, centrifuge the mixture, use a continuous flow centrifuge while maintaining the temperature in the range of two to eight degrees Centigrade to separate paste 70 from supernatant 72. The resultant supernatant (supernatant 72) contains essentially no IgG. Virtually all of the IgG of plasma 50 is now found in paste 70.

Figure 2:
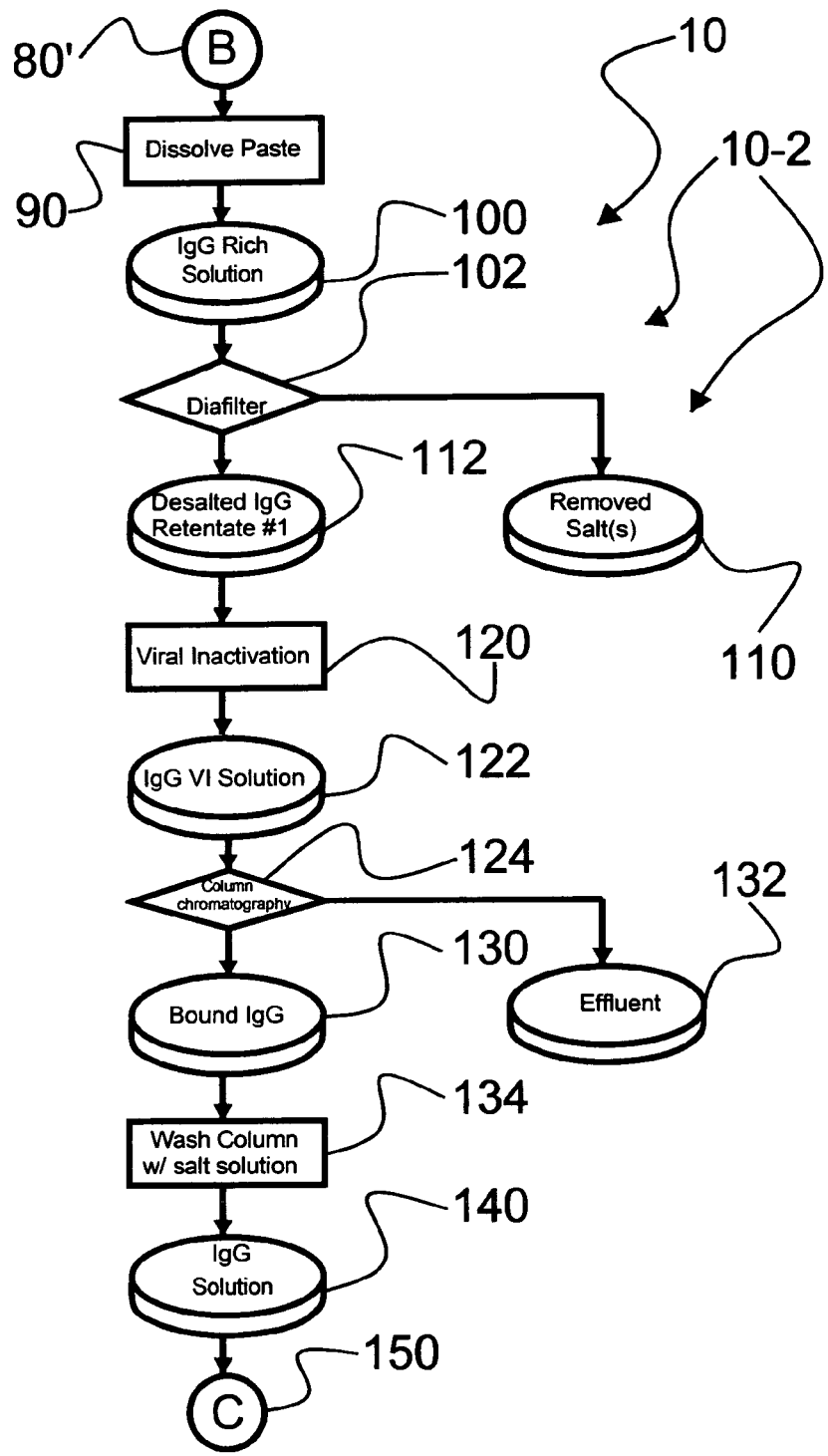
FIG. 2 is a flow diagram disclosing a series of steps which immediately follow the steps seen in FIG. 1.

Reference is now made to FIG. 2 as point 80 continues to point 80' for flow path portion 10-2 of flow path 10. Contents of paste 70 includes IgG, other serum proteins and sodium citrate. The sodium citrate (and/or other used salt or salts) must be removed from paste 70 to permit IgG to be isolated by ion exchange chromatography. First, paste 70 is liquified using purified water (of about four times the volume of paste 70) as step 90. Product of step 90 is an IgG rich solution 100. Initial conductivity of solution 100 is approximately 20 milliSiemens/centimeter (mS/cm).

Removal of sodium citrate (and/or other used salt or salts) is accomplished by continuous diafiltration using purified water as a solvent in step 102 which separates solution 100 into removed sodium citrate 110 and desalted IgG retentate 112. Note that this step should be consistently performed, independent of the selected at least one salt. Completion of step 102 is indicated when the conductivity of retentate 112 is reduced to 100-900 microSiemens/centimeter (uS/cm). For diafiltration in step 102, a Millipore (or comparable) diafiltration system equipped with 30 KD cut-off membranes may be employed.

Viral inactivation of IgG rich retentate 112, associated with step 120, may be accomplished as a double viral inactivation step involving a first solvent/detergent (S/D) method, followed by an augmented S/D method. The first method employs raising the temperature of retentate 112 to approximately twenty-seven degrees Centigrade (temperature may range from twenty-four to thirty degrees Centigrade). A sufficient volume of TRITON X-100® or TWEEN-80® is then added to make a one percent solution and sufficient Tri-N-Butyl Phosphate to make a three tenths of one percent solution to make a first S/D added mixture. The first method continues by incubating the first S/D added mixture at twenty-seven degrees Centigrade for three hours during which time lipid enveloped viruses are inactivated. From this point, procedures currently available, inactivation and fractionation processes may be employed. However, a currently preferred process is hereafter provided for completeness.

For step 120, a S/D concentrate may be made as follows:

Add 30 milliliters of Tri-N-Butyl Phosphate to 800 milliliters of purified water. Mix well. Add 100 milliliters of either TRITON X-100® or TWEEN-80® to the mixed solution. Again, mix well to provide a final, mixed S/D solution. Add enough purified water to bring the total volume of the final mixed solution to 1000 milliliters. One more time, mix well. So made, the final solution is a 10× concentrate. Add 100 milliliters of this concentrate to each 900 milliliters of retentate 112 to form the first S/D added mixture.

After three hours of incubation, add, to the solution resulting from the first S/D method, sufficient formaldehyde to make a three tenths of one percent solution and sufficient phenol to make a three tenths of one percent solution to form an augmented mixture to begin the augmented method phase of step 120. Incubate at approximately twenty-seven degrees for an additional three hours, after which time non-enveloped and enveloped viruses are inactivated.

For step 120, an "augmented" concentrate may be made as follows:

Add 13.4 milliliters of thirty-seven and one-half percent formaldehyde solution to 900 milliliters of purified water. Mix well. Add fifty grams of phenol (reagent grade) to this mixture. Again, mix well. Add enough purified water to bring the total volume of the "augmented" preparation to one thousand milliliters. Once more, mix well. This preparations contains 50,000 parts per million each of formaldehyde and phenol (five percent of each). Measure the volume of the first S/D added mixture. Add 167 milliliters of augmented concentrate to each 833 milliliters of first S/D added mixture to form the augmented mixture.

Step 120 is completed by cooling the processed augmented mixture to a temperature of two to eight degrees Centigrade. So cooled, the augmented mixture becomes IgG virus inactivated (VI) solution 122.

Alternatively, viruses may be removed by other methods (e.g., chromatography, nanofiltration, pasteurization), if desired.

Step 124 involves use of column chromatography to remove viral inactivation chemicals. Such may be accomplished by the following sub-steps:

1. Set up a short, wide column with TOYOPEARL® CM-650C resin. The TOYOPEARL® resin is a weak cationic exchange resin used to capture IgG in solution 122 while permitting other proteins from solution 122 to flow through the column. It is important that the conductivity of solution 122 be in a range of 100 to 900 microSeimens/centimeter (uS/em). (It is preferable that such conductivity is in a range of 400 to 600 micro-Seimens/centimeter.) IgG from plasma 50 binds to the exchange resin in the low ionic strength solution.

2. Introduce solution 122 into the exchange resin at a slow rate. Collect effluent liquid from the column and measure the effluent liquid at 280 nano-meters in a one centimeter silica cuvette in a high quality spectrophotometer. (As an example, a Beckman DU-7 with a deuterium light source may be used.) It should be noted that optical density of the effluent will increase as proteins are introduced into the resin column. Phenol in the viral inactivation solution (if used) also can increase measured optical density. After all of solution 122 has passed through the resin column and sterilants are washed from the column, begin collecting the effluent when measured optical density increases from its original value. A rise in optical density is indicative of protein in the effluent. After a period, optical density drops down to a level which is indicative of little or no protein in solution. At this point, collecting may cease. At this point, it is preferable to thoroughly wash the resin with deionized water. Bound material is IgG, identified along path 10-2 as bound IgG 130. Collected effluent from the column includes all of the protein from plasma 50 except for IgG. This effluent is effluent solution 132. It is recommended that serum protein electrophoresis be performed on effluent solution 132 to confirm that little or no IgG has been released into solution 132.

Depending upon size of the resin column, prepare a volume of two percent solution of sodium chloride. Application of the sodium chloride is used to effect release of attached IgG from resin particles. As is well-known in chemistry art, a two percent solution is made by mixing 20 grams of sodium chloride into one liter of deionized water. Sufficient volume of two percent sodium chloride solution should be made to equal about ten times the volume of the resin column.

For step 134, add the sodium chloride solution to the column, collecting effluent from the column. Concurrently, measure optical density of the effluent solution at 280 nanometers using a spectrophotometer with a one centimeter silica cuvette. Resultant optical density (OD) will be found to suddenly increase as IgG is uncoupled from the resin and delivered into the effluent. Collect all high OD measured solution. When the OD of the effluent drops to a lower (normal) range, cease collecting the solution. Resulting solution is IgG solution 140. Note that a high OD is indicative of protein content in solution, and that solution 140 may contain small amounts of IgM and IgA, which requires further removal. In addition solution 140 contains sodium chloride which must be removed before any pure IgG can be isolated.

Figure 3:
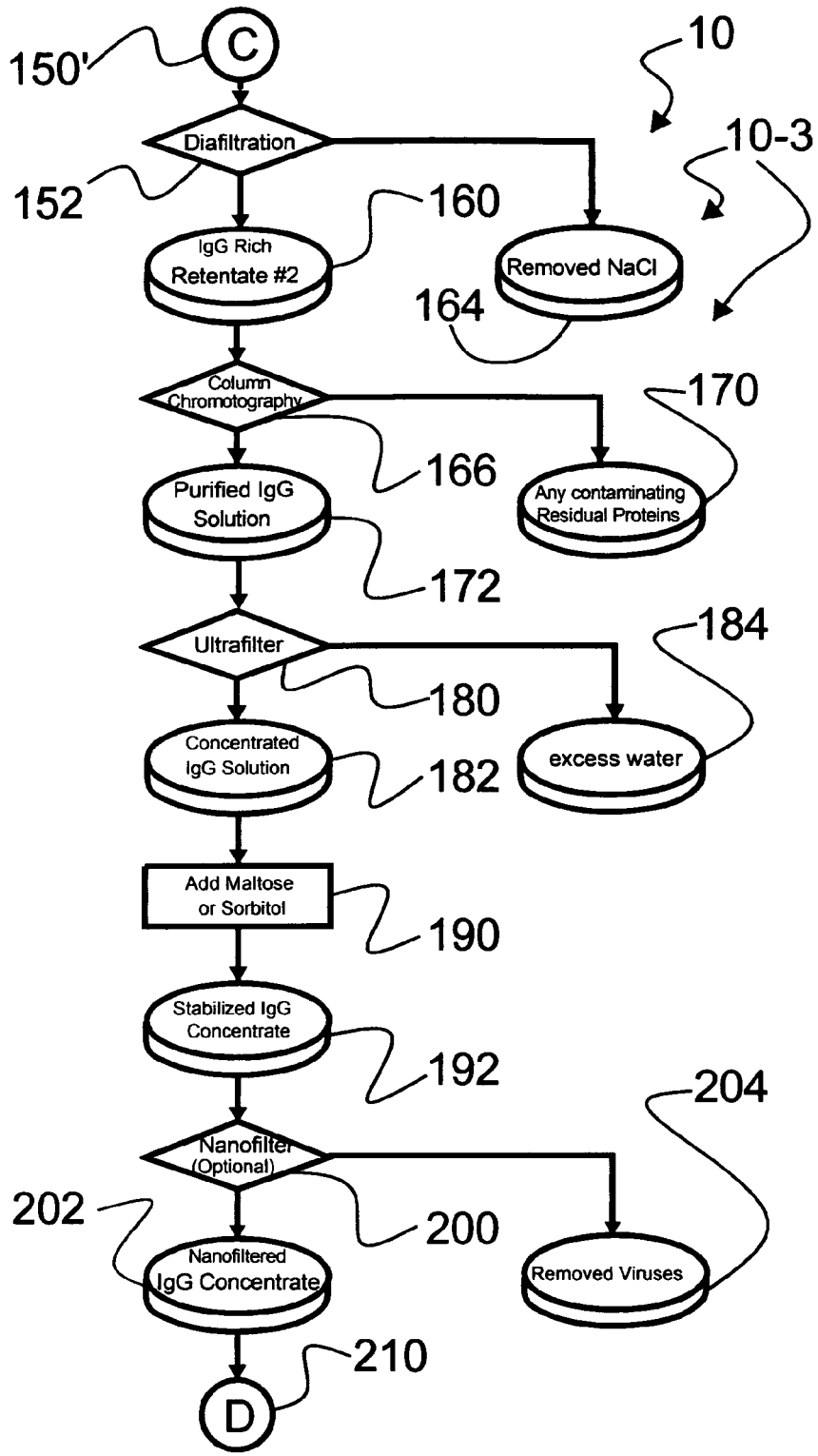
FIG. 3 is a flow diagram disclosing those procedural steps which immediately follow the steps seen in FIG. 2.

Reference is now made to continuation point 150 in FIG. 2 which continues to continuation point 150' in FIG. 3 for flow path portion 10-3 of flow path 10. Sodium chloride is preferably removed from solution 140 by continuous diafiltration employing a diafiltration system. Such may consist of a Millipore (or comparable) diafiltration system equipped with 30 KD cut-off membranes. As performed in step 152, the diafiltration solvent is purified water. As may be noted, initial conductivity of solution 140 is approximately fifty milliSiemens/centimeter (mS/cm). At completion of diafiltration, conductivity is reduced to 100-900 microSiemens/centimeter (uS/cm).

The products of diafiltration are an IgG rich retentate 160 and removed sodium chloride 164. It is recommended that serum electrophoresis be performed at this step in the process to confirm protein fractions in retentate 160.

Step 166 is a final step for purifying IgG rich retentate 160. For step 166, it is preferred to set up a short, wide resin column with TOYOPEARL® QAE-550C resin. Such resin provides a strong anionic exchange for capturing other proteins in IgG rich retentate 160, while permitting IgG in solution to flow through the column. It is important that conductivity of retentate 160 be in a range of 100 to 900 microSeimens/centimeter, and preferably, within a range of 400 to 600 microSeimens/centimeter. In this manner, IgG in retentate 160 will pass through the resins column in Step 166 without binding, while other proteins, including IgM and IgA, will bind to resin in the column and thus be removed from solution. In this manner, any contaminating residual proteins 170 are effectively separated from a purified IgG solution 172.

As the process is continuous, it is recommended that IgG solution 172 be collected and the OD measured at 280 mm. Collect the high OD effluent solutions. When the measured OD drops, cease collecting. The pooled solution is relatively dilute.

The pooled solution is concentrated using step 180 via ultrafiltration. For such ultrafiltration, a hollow fiber filter may be used, or a Millipore ultrafiltration system (Pellicon) or equivalent, (10K to 30K dalton retentation) to concentrate to a twelve percent IgG solution 182. Excess water 184 is removed in the process of step 180. The resulting twelve percent concentrate should have only a trace amount of sodium chloride and the pH should be approximately seven. Conductivity should measure about 100 to 900 microSiemens/centimeter.

To stabilize the twelve percent IgG solution 182, add (step 190) a maltose or sorbitol solution to dilute the twelve percent solution to exactly ten percent. The final ten percent solution (IgG solution 192) should contain approximately five percent maltose or sorbitol (whichever is used).

Optionally, to remove viruses 204 from IgG solution 192, nanofiltration may be performed by passing the ten percent solution 192 through a virus retaining membrane (step 200) to produce a nanofiltered concentrate 202.

Figure 4:
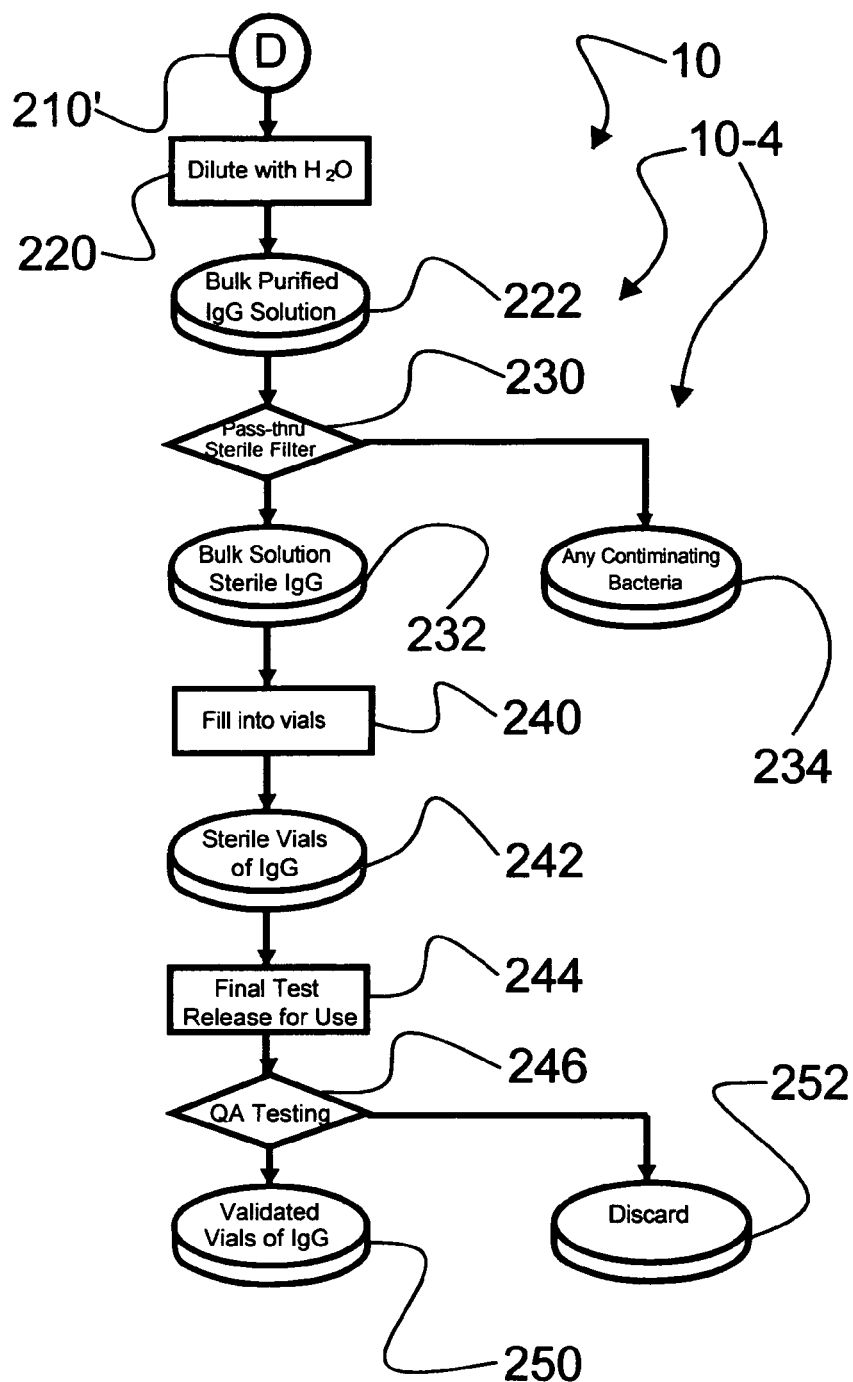
FIG. 4 is a flow diagram disclosing steps which immediately follow the steps seen in FIG. 3 to provide a useful product.

Reference is now made to continuation point 210' in FIG. 4, for flow path portion 10-4 of flow path 10, which continues from continuation point 210 in FIG. 3. As is standard procedure, (depending upon execution of prior option step 200) either stabilized IgG concentrate 192 or nano-filtered IgG concentrate 202 is diluted with deionized water in step 220 to produce a bulk purified IgG solution 222. Contaminating bacteria may be removed by passing solution 222 through a sterilizing filter in step 230 to produce a sterilized bulk IgG solution 232. Removed contaminating bacteria 234 may be disposed of by methods currently known in the art.

Resulting sterile solution 232 may be filled into vials per standard procedures in step 240 to produce a lot 242 of vials of solution 232. As required for quality assurance, final testing and inspection of lot 242 may be made in step 244 in cooperation with step 246 to produce a lot 250 of validated vials of solution 232, with any discard 252 being removed therefrom.

Reference is now made to FIG. 1 wherein flow chart 10-1 discloses steps for separating out a paste from which other products, e.g. Factor VII, von Willebrand Factor, and other clotting factors which may be fractionated, are seen. Steps associated with product 44 seen in FIG. 1 are optional and may be followed to produce a cryoprecipitate from which Factor VIII, von Willebrand Factor, and other clotting factors can be removed. In this case, procedure 40 is defined to gradually warm plasma 30 to zero to four degrees Centigrade. Such warming results in a thawed plasma in which a cryoprecipitate is suspended. Per step 42, the thawed plasma is centrifuged to yield the cryoprecipitate in the form of a paste 44. Paste 44 may be subsequently separated and processed by known methods to provide Factor VI, von Willebrand Factor, and other clotting factors. The remaining separated material, named cryo-poor plasma 50, is processed as disclosed supra.

Results of a Fractionation Procedure Performed According to the Instant Invention:

In order to show the efficacy and precision of separation of steps of the instant invention disclosed herein, the following results, using sodium citrate, have been extracted from a laboratory report, dated Aug. 8, 2005.

In the procedure, fresh frozen human plasma was used. As is typical in such procedures, a pool was made from four to eight bags of thawed plasma (see step 40, FIG. 1). Commercial equipment available from Beckman-Coulter was used to evaluate various fractions as they became available. The Beckman, "Appraise", densitometer was used to scan the Beckman agarose gels for serum protein electrophoresis as part of a Paragon Electrophoresis System. For each fraction made from the pool, between three and five gel slits were loaded with five microliters of product. Results were averaged to obtain a better representative result for each fraction. Such results are found in tables provided hereafter.

The gels were electrophoresed for twenty-five minutes at 100 VDC at a pH of 8.6 and later stained with a Paragon blue stain. The Appraise densitometer was used to scan the stain-dried gels at a wavelength of 600 nanometers twice for each gel slit (ten gel slits per gel were used). An average graphic representation of the distribution of five different protein fractions, based upon density of attached dye as well as a numeric presentation of each fraction was derived. The numeric presentation was based upon a computer analysis of peaks and valleys of generated graphs at selected locations within the gel pattern as occurred between the anode and cathode on each gel. Presentation values were totaled and dye percentage was divided by the total dye amount to provide a percentage for evaluation. Note that the grand total, summing each individual blood fraction always equals one hundred percent.

As seen in Table II below, the five different protein fractions are identified as: Albumin, Alpha 1, Alpha 2, Beta and Gamma globulin. Before fractionation, a sample was removed from the pool and electrophoresed to determine the average fractional values of each fraction before beginning fractionation. Representative results for the average base pool material are listed below as percentages of whole plasma:

TABLE II

| | Percentage content of each fraction | | | | |
| --- | --- | --- | --- | --- | --- |
| | Albumin | Alpha 1 | Alpha 2 | Beta | Gamma |
| Base plasma | 61.2 | 7.1 | 9.7 | 13.0 | 8.9 |

Plasma (i.e., plasma 50) from the pool was treated with the addition of a volume of fifty percent sodium citrate to a volume of plasma to make a twelve percent solution of sodium citrate (step 54). This mixture was stirred for sixty minutes at two to eight degrees Centigrade and was then centrifuged (Step 56) for sixty minutes at two to eight degrees Centigrade. The resulting supernatant solution 60 was measured. The remaining paste 62 was weighed and put into solution by addition of deionized water.

The two solutions (60 and 62 (dissolved)) were electrophoresed using procedures cited supra, the results of which are summarized in Table III, below:

TABLE III

Resulting percentage concentrations

|  | Albumin | Alpha 1 | Alpha 2 | Beta | Gamma |
|---|---|---|---|---|---|
| 12% Paste 62 (dissolved) | 67.8 | 2.7 | 9.1 | 20.4 | nd* |
| 12% Supernatant 60 | 28.6 | 1.5 | 10.7 | 40.3 | 16.1 |

*nd = none detected

There was no gamma globulin found in Paste 62 (dissolved). However, there was gamma globulin found in Supernatant 60.

Next, sufficient fifty percent solution sodium citrate was added to supernatant 60 (step 64) to obtain a final mixture that contained twenty-two percent sodium citrate. This solution was also stirred for sixty minutes at two to eight degrees Centigrade. After centrifuging (see step 66) for sixty minutes at two to eight degrees Centigrade, the resulting supernatant solution 72 was measured The remaining paste 70 was weighed and put into solution (step 90) by the addition of deionized water (four times weight of paste 70 in milliliters) to form IgG rich solution 100. Samples of supernatant 72 and IgG rich solution 100 were electrophoresed by the procedure cited supra, the results of which are summarized in Table IV below:

TABLE IV

Percentage concentrations of indicated solutions

|  | Albumin | Alpha 1 | Alpha 2 | Beta | Gamma |
|---|---|---|---|---|---|
| 22% Supernatant 72 | 82.4 | 13.9 | 3.6 | nd* | nd* |
| 22% Sol. 100 (dissolved) | 16.7 | 1.3 | 10.5 | 32.5 | 39.0 |

*nd = none detected

There was no gamma globulin found in supernatant 72. However, there was gamma globulin found in IgG rich solution 100.

The 22% supernatant fluid (which contained mostly albumin) contained essentially no beta and gamma globulin (i.e., none of such that was detected). The twenty-two percent paste solution 100 contained the gamma globulin of interest for further fractionating to produce intravenous gamma globulin for injection. Note also that, in step 90, time should be allowed for the paste to solvate prior to performing electrophoresis. In the experimental process, a plasma fraction between twelve percent and twenty-two percent sodium citrate was selectively isolated out for use in this isolation procedure.

To remove sodium citrate (step 102) trapped in the twenty-two percent paste solution, a Pellicon unit was selected to diafilter solution 100. On the average, about seven times the volume of solution 100 was required to diafilter the sodium citrate and bring conductivity of the resulting solution down to a range between 400 and 800 microSiemens/centimeter (uS/cm), before performing any column work.

After diafiltration, the desalted protein solution 112 was treated electrophoretically to determine any changes or losses as a result of diafiltration step 102. Because sodium citrate was removed, protein movement in the electrophoretic pattern was changed somewhat through lack of interference with a contained salt. The resulting pattern was somewhat longer than a high salt concentration pattern. This elongated pattern allowed IgG to separate more readily from beta globulin with a resulting increase in measured percentage as seen in Table V, provided below:

TABLE V

Percentage content of diafiltrate fractions

|  | Albumin | Alpha 1 | Alpha 2 | Beta | IgG |
|---|---|---|---|---|---|
| Solution 112 | 16.6 | 1.5 | 9.9 | 26.9 | 45.2 |

As seen in Table V, approximately forty-five percent of solution 112 was gamma globulin and solution 112 exhibited better separation in the electrophoresis pattern. Note, that the beta fraction went down with better separation in the electrophoresis pattern.

At this point, various currently employed methods could have been used to purify the gamma globulin in solution 112. For that reason, the completion of this experiment could have varied from steps seen in FIGS. 2-4. In the case of this experiment, the solution was first treated with a Solvent/Detergent solution of three hours at twenty-seven degrees Centigrade. Then an augmented sterilization solution, performed according to U.S. Pat. No. 6,881,573, titled AUGMENTED SOLVENT/DETERGENT METHOD FOR INACTIVATING ENVELOPED AND NON-ENVELOPED VIRUSES, issued to Allan L. Louderback, filed Sep. 12, 2003, was added to the mixture and further incubated for an additional three hours at twenty-seven degrees Centigrade. This dual inactivation treatment of the dialyzed diafiltered solution inactivates both enveloped and non-enveloped viruses.

The sterile treated solution was transferred to an ion exchange column loaded with TOYOPEARL® CM-650C resin. The resin adsorbed gamma globulin and allowed all of the other proteins present in solution to flow out in effluent from the column. After adding the solution to the column and adjusting the column flow to slowly drip out through the effluent end, effluent solution was measured at 280 nanometers to determine when all free proteins and sterilants had been transported through the column. Afterward, the column was washed with a two times volume of purified water to assure that the effluent has a very low measured optical density at 280 nanometers.

A two percent solution of sodium chloride was then dispensed onto the top of the column and allowed to percolate through the column. Gamma globulin which was adsorbed by resin particles was freed to flow out of the column into a receiving vessel.

Collected effluent from the column with purified water (labeled as Purified Water) and effluent from the column with the two percent solution (labeled as two percent NaCl) were tested electrophoretically to show the result of selected isolation and release of gamma globulin from the resin particles. Results of this step is summarized in Table VI, seen below:

TABLE VI

Resulting percentage fractions

|  | Albumin | Alpha 1 | Alpha 2 | Beta | IgG |
|---|---|---|---|---|---|
| Purified Water | 26.0 | 2.7 | 15.2 | 57.0 | nd* |
| Two Pecent NaCl | nd* | nd* | nd* | 1.9 | 98.1 |

*nd = none detected

Note that more than 98% of the gamma globulin was isolated in the first resin treatment. The value for beta globulin of 1.9% may be the result of an application spot when applying solution to gel. The two percent sodium chloride solution contained the gamma globulin (IgG) and, perhaps, with larger pools of plasma, may contain some IgA and IgM globulins which should be removed.

The two percent sodium chloride solution was therefore diafiltered to remove the sodium chloride for a next column treatment. Diafiltration was again performed by passing the solution though a Pellicon unit whereby the salt was removed, yielding a final product which had a conductivity of 400 to 800 microSeimens/centimeter (uS/cm). Note that it likely takes about six volumes of dionized purified water to diafilter the two percent solution.

As a final step, a column was filled with TOYOPEARL® 560-C resin and the desalted solution was added to the top of the column and allowed to slowly percolate through the column. In this column, IgG flowed right through the resin and all other proteins attached to the resin (e.g., IgA and IgM) to yield a final effluent from the column (solution 172) that was 100% IgG in an aqueous base. The effluent tested is seen in Table VII below:

TABLE VII

Percentage content of final solution

| | Albumin | Alpha 1 | Alpha 2 | Beta | IgG |
|---|---|---|---|---|---|
| Solution 172 | nd* | nd* | nd* | nd* | 100 |

*nd = none detected

Following the pathway of Charts 10-1 and 10-2, other experiments have been performed using various salts in fractionating fresh frozen plasma Steps 52, 54 and 64 were repeated using the various salts to complete the fractionation procedure in the two stages as outlined supra. As seen in Table VII, below, and consistent with the method disclosed for sodium citrate, first steps 52 and 54 comprised mixing a set volume of plasma with a first predetermined volume of concentrated salt solution, where possible. Where it was not possible to achieve a necessary concentration of salt by dissolving salt in water, dry salts were simply added to achieve the desired concentration, by weight.

The first predetermined volume of salt solution was twelve percent by weight. Reaction mixing followed at two to eight degrees Centigrade for one hour. After reaction mixing, the resulting mixture was spun down at two to eight degrees Centigrade at 4500 rpm for one hour. A first supernatant fluid 60 overlying a paste precipitant 62 was gently poured off and collected. Note that the first supernatant fluid 60 contained a twelve percent solution, by weight, of the salt used. Generally, the resulting paste precipitant 62 was diluted with a percentage by weight of deionized water (usually four times the weight of collected precipitant 62) and stored at two to eight degrees overnight for further analysis.

Per step 64, volume of supernatant 60 was measured and an amount of concentrated salt solution was added to raise the concentration of salt to a level of twenty-two percent, by weight. The resulting composition was mixed for one hour at two to eight degrees Centigrade and then refrigerated overnight. The following morning, the composition was mixed again briefly for about five minutes and then centrifuged for one hour at 4500 rpm at two to eight degrees Centigrade. Any supernatant, supernatant 72, was poured off and saved for any desired further processing. Paste 70, the target of this procedure, after separation from supernatant 72, was weighed and diluted (redissolved per step 90, by adding an amount of deionized water calculated to be about four times the weight of paste 70).

The above disclosed procedure was repeated for both organic and inorganic salts in various combinations. Table VIII, shown below, provides results of the procedure as determined by serum electrophoresis performed using the Beckman-Coulter system, Results of the electrophoresis were scanned with the Beckman-Coulter scanner and are presented as the percentage of protein at each of five levels, name as albumin, alpha-1, alpha-2, beta and IgG. The total for each scan, by the Beckman algorithm, approximates 100% when summed

TABLE VIII

Serum Electrophoresis Results of Salt Fractionations - showing % of each fraction

| Expt. Num | Stage 1 12% | Stage 2 22% | Albumin | Alpha1 | Alpha2 | Beta | IgG |
|---|---|---|---|---|---|---|---|
| 1 | Ammonium sulfate | Ammonium sulfate | 18.1 | 1.9 | 25.6 | 24.6 | 29.9 |
| 2 | Sodium citrate | Sodium citrate | 19.4 | 1.4 | 10.1 | 35.4 | 33.2 |
| 3 | Ammonium sulfate | Sodium citrate | 17.0 | 1.6 | 9.6 | 26.4 | 45.5 |
| 4 | Sodium Citrate | Ammonium sulfate | 17.9 | 1.6 | 12.6 | 24.7 | 43.2 |

There was no IgG found in the paste 62 nor in the supernatant 72. All of the IgG is found in paste 70. One should not be confused because values are higher for IgG for mixed organic (sodium citrate) and inorganic (ammonium sulfate) salts. Such is a result of a differential extraction of other proteins from the plasma. Some proteins have different precipitation patterns with different salts. The important result is that substantially all of the IgG is found in the paste 70.

Results of a Procedure Performed Via the Instant Inventive Method Using Ethanol

Surprisingly, it has been found that ethanol may be used within the scope of the instant invention as a fractionation compound. It should be noted that this use of ethanol is markedly distinct from contemporary and historical methods employing ethanol in blood fractionation.

The method was tested and recorded in experimental laboratory notebooks, dated Dec. 8, 2005, using one frozen FFP-plasma bottle to provide a comparison with experiments disclosed supra. In this experiment, ethanol was used in concentrations measured by percentage in the same manner disclosed for salts. Thus, a ninety-five percent ethanol solution was diluted to prepare a fifty percent ethanol solution (one hundred and five milliliters of ninety-five was added to ninety-five milliliters of deionized water). So, prepared, the solution was placed in an ice bath to lower the temperature to five degrees Centigrade.

Per step 54, sixty-three milliliters of the fifty percent ethanol solution was added to two hundred milliliters of FFP-plasma (from the spare) which was kept at five degrees Centigrade. The resulting solution (i.e. twelve percent ethanol) was stirred for one hour in an ice bath (at two to eight degrees Centigrade). After stirring, per step 56, the solution was spun down for one hour using a Beckman J-6 centrifuge (4500 rpm), while the temperature was maintained at two to eight degrees Centigrade. The supernatant 60 was poured off and the so separated paste 62 was measured.

The volume of supernatant 60 was 260 milliliters. Weight of paste 62 was 3.823 grams. Paste 62 was rehydrated with water (a four times volume, i.e. 15.3 milliliters and mixed well. Paste 62 showed a typical clot-like precipitate. Final diluted volume was 18 milliliters.

Supernatant 60 was displaced into an ice bath. Additional fifty percent ethanol (ninety-three milliliters) was added to supernatant 60 to increase ethanol concentration to twenty-two percent, by weight (step 64). This resulting solution was stirred for one hour at two to eight degrees Centigrade, and then stored overnight in a refrigerator (at two to eight degrees Centigrade).

The stored solution was stirred for about five minutes when taken from the refrigerator, then displaced into a centrifuge bottle and spun at 4500 rpm for one hour at two to eight degrees Centigrade (per step 66). A supernatant 72 was poured off and a paste 70 was collected. It was noted that paste 70 was bright yellow in color. (Most commonly, paste 70 is a gray-white color when produced using salts). Though not known exactly, it was suspected that the yellow color was due to billirubin and other chromogens being extracted from the plasma by the ethanol. Library samples were made at each fractionation step.

Supernatant volume was measured (336 milliliters) and stored at five degrees Centigrade. Paste 70 weighed 8.583 grams. Paste 70 was rehydrated via a four times volume of deionized water (34.3 milliliters), mixed well and stored overnight at two to eight degrees. It is interesting to note the unexpectedly high amount of IgG in paste 70 when solvated.

Measured results are summarized in Tables IX, X and XI, below:

TABLE IX

Serum Electrophoresis: Showing percent of each fraction.

| | Albumin | Alpha-1 | Alpha-2 | Beta | IgG |
|---|---|---|---|---|---|
| Paste 62 | 39.2 | 2.2 | 15.4 | 33.4 | 9.7 |
| Supernatant 72 | 73.7 | 9.1 | 8.3 | 8.9 | — |
| Paste 70 | 6.7 | 2.8 | 17.2 | 6.7 | 66.6 |

TABLE X

Volume amounts of final fractionation.

| Sample | Weight - gm | Volume - ml |
|---|---|---|
| FFP-plasma | | 200 |
| Paste 62 | 3.823 | 18 |
| Supernatant 72 | | 336 |
| Paste 70 | 8.583 | 40 |

TABLE XI

Protein Results

| | ml | gm/dl - protein | gm/liter - protein | gm/liter - IgG |
|---|---|---|---|---|
| FFP-Plasma | 200 | 6.05 | 60.5 | 6.7 (11% - IgG) |
| Paste 62 | 18 | 1.09 | 0.98 | 0.5 |
| Supernatant 72 | 336 | 2.73 | 45.9 | — |
| Paste 70 | 40 | 4.75 | 9.5 | 6.3 |

No electrophoresis was run on the initial base material. However, note that there is about 6.7 grams of IgG per liter of plasma. If the IgG in past 62 is added to IgG in paste 70, the total of 6.8 agrees well with the anticipated 6.7 grams per liter.

The invention may be embodied in other specific forms without departing from the spirit or essential characteristics thereof. The present embodiment is, therefore, to be considered in all respects as illustrative and not restrictive, the scope of the invention being indicated by the appended claims rather than by the foregoing description, and all changes which come within the meaning and range of equivalency of the claims are, therefore, intended to be embraced therein.

What is claimed and desired to be secured by Letters Patent is:

1. A method of deriving a blood product from a blood based material, comprising:
    producing a euglobulin-depleted intermediate from the blood based material by adding a first salt to a previously cryo-processed quantity of blood based material, in an amount that achieves a first salt concentration in the euglobulin-depleted intermediate;
    adding a second salt to the euglobulin-depleted intermediate to form a precipitate having a second salt concentration greater than the first salt concentration;
    diluting the precipitate to form a second intermediate; and
    filtering out at least some of the added salt from the second intermediate to produce a composition that includes the blood product.

2. The method of claim 1, wherein the first salt is selected from the group consisting of a citrate, an acetate, and a gluconate.

3. The method of claim 1, wherein the step of producing a euglobulin-depleted intermediate comprises adding a sodium citrate solution to the blood based material.

4. The method of claim 1, wherein the first salt is selected from the group consisting of a sulfate and a chloride.

5. The method of claim 1, wherein the euglobulin-depleted intermediate is substantially euglobulin free.

6. The method of claim 1, wherein the step of producing a euglobulin-depleted intermediate comprises adding a total of 11-13 wt % of the first salt to the blood based material.

7. The method of claim 1, wherein the step of producing a euglobulin-depleted intermediate is accomplished without addition of alcohol.

8. The method of claim 1, wherein the step of adding a second salt to the euglobulin-depleted intermediate comprises adding a total of 21-23 wt % of the second salt and optionally at least one other salt to the euglobulin-depleted intermediate.

9. The method of claim 1, further comprising producing a supernatant from the euglobulin-depleted intermediate, and deriving a commercial quantity of at least one of albumin and alpha-1-antitripsin from the supernatant.

10. The method of claim 1, wherein the step of diluting the precipitate comprises adding water to the precipitate.

11. The method of claim 1, wherein the step of filtering out at least some of the salt comprises using a diafiltration membrane.

12. The method of claim 1, further comprising processing the second intermediate to extract a commercial quantity of IgG.

* * * * *